US005842969A

United States Patent [19]

Vikhrev

[11] Patent Number: 5,842,969

[45] Date of Patent: Dec. 1, 1998

[54] METHOD OF SEXUAL DISHARMONY CORRECTION DURING THE SEXUAL ACT

[76] Inventor: Gennady Alexeevich Vikhrev, Bolshoi Kozikhinsky pereulok, 15, korpus 2, kv. 9, Moscow, Russian Federation

[21] Appl. No.: 796,279

[22] Filed: Feb. 7, 1997

[51] Int. Cl.$^{6}$ ..................... A61F 5/00

[52] U.S. Cl. ..................... 600/38; 128/843

[58] Field of Search ..................... 128/842, 843, 128/844, 918; 600/38–40; 604/347–353

[56] References Cited

U.S. PATENT DOCUMENTS

| | | | |
|---|---|---|---|
| 3,504,665 | 4/1970 | Bakunin et al. | 128/36 |
| 3,809,090 | 5/1974 | Poviacs | 128/294 |
| 4,512,342 | 4/1985 | Zaneveld | 128/843 |
| 4,957,104 | 9/1990 | Zorgniotti | 600/40 |
| 5,471,997 | 12/1995 | Thompson | 128/843 |

FOREIGN PATENT DOCUMENTS

| | | |
|---|---|---|
| 2033119 | 4/1995 | Russian Federation . |

*Primary Examiner*—Michael A. Brown

*Attorney, Agent, or Firm*—Ostrolenk, Faber, Gerb & Soffen, LLP

[57] ABSTRACT

The method of correciton of sexual disharmony brings about the stimulation of feminine erogenous zones during the sexual act by way of an aimed mechanical action on the area of clitoris and of the vagina of ball-like elements made from biologically inert materials of 8 to 15 mm in diameter implanted in a numbers of 1 or 2 into the edges of the slit prepuce or under the skin of the penis in a number of 1 to 3 of 5 to 10 mm in diameter and also by the ends of a synthetic thread of 10 to 15 mm long of 0.5 to 1 mm in diameter fixed to the frenulum of the prepuce by 4 to 5 knots through it of 1 to 1.5 mm in diameter.

11 Claims, 1 Drawing Sheet

METHOD OF SEXUAL DISHARMONY CORRECTION DURING THE SEXUAL ACT

FIELDS OF THE INVENTION

The invention belongs to the medical area, i.e. to sexology and to that part of it which has to do with the correction of disharmony during the sexual act.

One of the reasons of sexual disharmony between partners is the presence of disturbances in the stimulation of feminine erogenous zones. As a result of this, women do not reach orgasm at all or have it late, are sexually unsatisfied and, as a result, psychologically and physically disturbed.

DESCRIPTION OF THE PRIOR ART

A method was offered to correct sexual disharmony which was based on the stimulation of feminine erogenous zones during the sexual act which included the stimulation of the clitoris by way of a vibrator (U.S. Pat. No. 3,504,665). But a special device must be used provoking inconveniences during the natural sexual act.

Another method of correcting sexual disharmony is by means of the stimulation of feminine erogenous zones with the help of a special masculine contraceptive with protuberances on its surface (U.S. Pat. No. 3,809,090). But the technical construction of this device does not give the possibility to activate the feminine erogenous zones of the clitoris in full measure.

Finally, another method of correciton of sexual disharmony which makes it possible to stimulate feminine erogenous zones during the sexual act is with the help of ball elements which have been implanted into the prepuce for permanent use (U.S. Pat. No. 2,033,119). This method can be applied as follows under local anaesthesia into the area of the front of the prepuce formed by the external and the internal tissues a slit of the skin is performed on the external tissues of the prepuce. The slot is used to form a channel and a cavity between the two tissues, and a ball-like element is implanted there. The edges of the wound formed by the external tissue are sewn together. This method has been conceived to achieve the implantation of ball elements of 5 to 15 mm of in diameter and has become an effective method for the stimulation the erogenous zones of the clitoris and the vagina during the sexual act. But it was noted in clinical practice that depending on the individual anatomical condition of the patients prepuce, during the implantation of ball elements of the 8 to 15 mm diameter the danger of narrowing the prepuce and developing phimosis emerges. Moreover, in some cases for medical and religious reasons the prepuce is cleaved, and this makes it impossible to use it as an anatomical object of the implantation of ball-like elements.

SUMMARY OF THE INVENTION

One aim of the invention is the exclusion of the danger of narrowing the prepuce and of developing phimosis.

The second aim is to make possible the correction of sexual disharmony in patients whose prepuce has been cleaved.

The third aim is to make more effective the correction of sexual disharmony during the sexual act.

These aims are achieved by way of correcting sexual disharmony during the sexual act through the following stages:

local anaesthesia of part of the prepuce;

the cleaving of the prepuce on the aforesaid part lengthwise from its free part into two so as the preputial sack formed by the external and internal tissues of the prepuce is divided into two parts—the right and the left;

the formation in each of the parts of a cavity by way of drawing apart the external and internal tissues;

the introduction into at least one of the cavities of one ball elements at a distance of at least 5 to 7 mm from the edge of the cut;

suturing of the wound formed by the aforesaid external and internal tissues on each of the edges where the cut on the preputial sack is made with the formation of two shreds of the aforesaid prepuce with the implantation into at least of them of at least one ball element.

Preferentially two ball elements are implanted, one into each of the aforesaid shreds of the preputial sack.

For the implantation ball elements of 8 to 15 mm in diameter are used.

It is desirable that the ball elements be fixed after introduction by $\pi$-like suture, so that they cannot be dislocated to the edge of the above mentioned shred.

The correction of sexual disharmony during the sexual act in patients whose prepuce has been cleaved is, according to the invention carried out in the following way:

under local anesthesia of the penis on the section on the medium line at a distance from the head of the penis of 5 to 15 mm;

the cleavage of the skin surface on the aforesaid section of the penis lengthwise on the projection of the medium line at a distance of 8 to 10 mm from the head of the penis;

the formation of a channel and of a cavity under the skin by way of surgical access through the afore-said cleavage of the left and to the right of it;

the introduction into the aforesaid cavity of at least one ball element at a distance of at least 5 to 7 mm from the mentioned line of the aforesaid cleavage of the skin;

a stitching of the edges of the wound formed by the mentioned cleavage of the skin.

It is desirable to use for the aforesaid implantation the mentioned ball elements of 5 to 10 mm in diameter.

It is preferable to fix each element by way of a-like suture which would permit to prevent dislocation of the elements to the edge of the wound.

On top of this, multiplication of the effect of the correction of sexual disharmony during the sexual act is achieved according to the invention by way of:

local anesthesia of the frenulum of the prepuce of the patients; penis;

It is possible to form the mentioned permanent aperture by way of:

pincing the tissues which form the frenulum with the help of an injection needle;

the introduction through the hole formed as a result of this of a synthetic thread of 1–1.5 mm in diameter;

the pulling out of the injection needle and of the synthetic thread after the healing of the edges of the formed permanent cavity.

The method according to the invention makes it possible to carry out the correction of sexual disharmony, the ensuring of orgasm in women by way of an effective stimulation of erogenous zones during the sexual act by way of widening the surface of simultaneous contact between the erogenous zones of the clitoris and of the vagina and of the masculine penis. The effect of a mechanical pressure on the erogenous zones is achieved by the edges of the cleaved prepuce and by the implanted ball elements of 8 to 15 mm in diameter. If the prepuce is absent then the ball-like elements of 5 to 10 mm in diameter can be implanted under the skin of the penis. To achieve feminine orgasm it is also proposed to use the effect of mechanical pressure on the erogenous zones of the clitoris and of the vagina of a synthetic thread 10 to 15 mm long, which are temporarily fixed onto the frenulum of the prepuce of the penis through a specially formed permanent aperture of 1 to 1.5 mm in diameter.

BRIEF DESCRIPTION OF THE DRAWINGS

Following is a description of the variants of the realisation of invention and the blueprints on which.

DETAILED DESCRIPTION OF THE INVENTION

Figure 1:
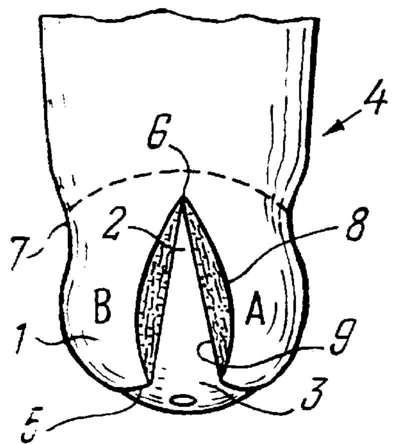
FIG. 1—a schematic image of the penis with the prepuce cleaved.
Figure 2:
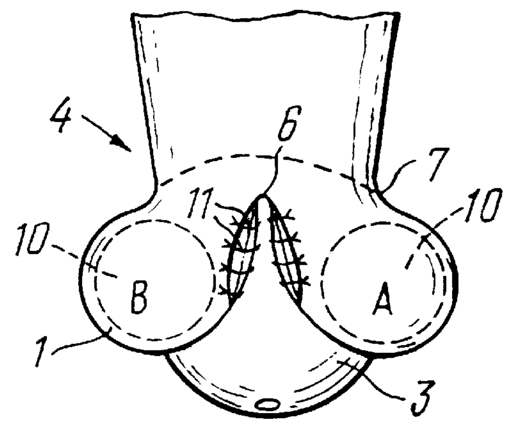
FIG. 2—as in FIG. 1 after the implantation into the prepuce of 2 ball-like elements.

The correction of sexual disharmony during the sexual act according to the invention is carried out in the following way. Under local anesthesia 3 to 5 ml of 0.5% novocaine solution is introduced into the prepuce I (FIG. 1,2), a skin slit 2 across the middle line of the front surface of the head 3 of the penis 4 is made, the prepuce I is slit lengthwise from its free edge 5 to the place 6 of its fixation at the neck 7 of the head 3 of the penis 4, the external 8 and internal 9 skin of the prepuce I is slit across the the length of it so that the preputial sack formed by the prepuce I is slit into two halves forming two parts: the right A and the left B. In each A and B of these the external and internal 8 and 9 skin of the slit edges of the prepuce I are divided forming a cavity. Into each cavity limited by the walls of the two pieces-right and left—one ball element 10 of 8 to 15 mm in diameter is implanted at a distance of 5 to 7 mm from the edges of the wound. Sutures 11 are stitched through the entire length of the wound formed by the slit edges of the preputial sack. The corresponding external and internal skins 8 and 9 of the prepuce I are sewn together along the entire wound with the formation of two pieces A, B of the prepuce with the implanted ball 10 elements. For the implantation, elements of a round form are used made from biologically inertial materials such as silicone rubber or ftoroplast. Additionally each ball-like element 10 implanted into the slit piece A and B of the prepuce I is fixed by π-like temporary sutures to prevent their dislocation to the edges of the wound during the healing period.

Figure 3:
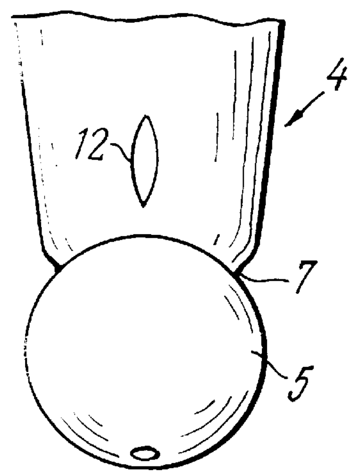
FIG. 3—a schematic image of the penis with the skin cut across the middle line.
Figure 4:
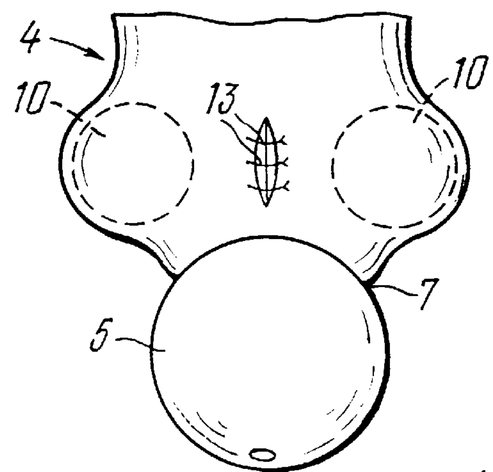
FIG. 4—as in FIG. 3 after the implantation of 2 ball-like elements.

The implantation of ball-like elements 10 (FIG. 3,4) under the skin of the penis 4 is also performed under local anesthesia which includes the introduction of 3 to 5 ml 0.5% novocaine solution. A skin slit 12 of 5 to 10 mm in length is performed lengthwise on the projection of the middle line of the front face of the body of the penis 4, 8 to 10 mm away from the neck 7 of the head 3 of the penis. The novocaine solution introduced under the the skin with the anesthesia plays the role of the hydraulic preparation of the tissues. In the place where the ball elements area to be implanted under the effect of novocaine hydraulics the parts of the skin are lifted from the under-skin cellular tissue and the superficial fascia of the penis. A narrow clutch is introduced into the wound with the help of this clutch and cavity for further implantation of the ball elements 10 channel use formed under the skin. As corresponding to the projection of middle line which is situated on the front surface of the penis 4, the channel and the cavities go to the left and to the right of the wound. Through a slit 12 in the skin into each of the formed channels and the cavities to the right and to the left the ball elements 10 are introduced at a distance of not less than 5 to 7 mm from the edges of the wound. The ball element 10 implanted under the skin is limited by its the sides and the foundation is the friable under-skin cellular tissues and the superficial fascia of the penis 4. The diameter of the implanted ball elements 10 is 5 to 10 mm. The edges of the wound are stitched with sutures 13 and additionally each ball-like element 10 implanted under the skin is fixed by π-like sutures (not demonstrated on the drawing) to prevent their dislocation to the edges of the wound during the period of healing.

In both the variants described, the sutures are taken off at 8 to 10 days after surgery and the sexual act is possible 2 to 3 weeks after that. The number of implanted ball-like elements and their diameter are determined by the anatomical characteristics of the penis.

Figure 5:
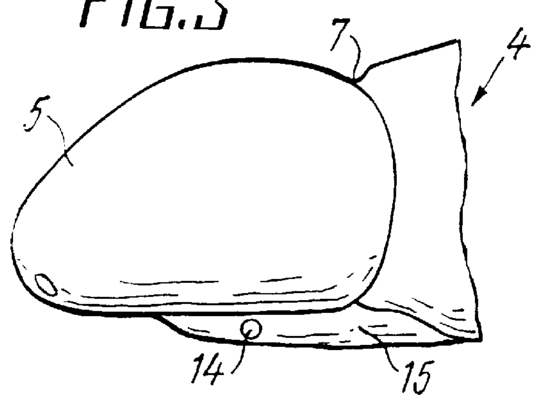
FIG. 5—a schematic image of the head of the penis with the hole in the frenulum of the prepuce.
Figure 6:
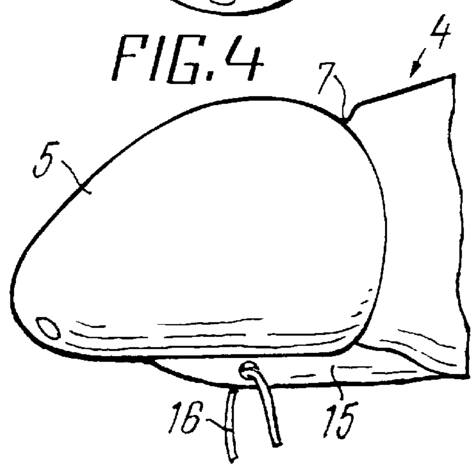
FIG. 6—as in FIG. 5 with the synthetic thread pulled through the hole.

Local anesthesia is also used to create a permanent aperture 14 (FIG. 5,6) in the frenulum 15 of the prepuce—a length wise fold formed by the skin surface of the prepuce in the place where it is attached to the lower surface of the head 3 of the penis 4. An aperture 14 of 1 to 1.5 mm in the frenulum 15 of the prepuce is created by way of pincing the tissues which form i.e. by different manipulations used in plastic surgery ranging from a simple injection needle to laser beam. The direction of the pincing tissues by the injection needle is transverse as corresponding to the frenulum 15 of the prepuce going lengthwise. Into the hole formed by the injection needle, a synthetic thread 16 of 1 to 1.5 mm in diameter is introduced, then the needle is pulled away, and a synthetic thread passing through the aperture 14 in the frenulum 15 of the prepuce is fixed by 4 or 5 knots. The synthetic thread 16 is withdrawn as a rule 2 weeks after the formation of the aperture 14 in the frenulum 15 of the prepuce. The aperture 14 formed in the described way of 1 to 1.5 mm in diameter in the frenulum 15 of the prepuce make it possible to fix temporarily to it the ends of a synthetic thread 10 to 15 mm long. These free ends of the thread (the "whiskers") in contact with the erogenous zones of the clitoris and of the vagina has a strong stimulating effect on the female erogenous zones and this in turn strengthen or brings about the orgasm in the female partner during the sexual act. The ends of the synthetic thread can be cut off and once again fixed to the frenulum 15 of the prepuce through the formed aperture 14 by the patient himself if necessary.

The possibility of the effectuation of the aforesaid aim is reaffirmed by the following concrete examples based on the use of this method.

EXAMPLE 1.

The patient is 44 years old. Has been divorced after 11 years of married life as a result of sexual disharmony; the wife did not experience orgasm during the sexual act.

During the last 3 years this patient has noticed an absence of orgasm in 75% of the cases when he had normal sexual relations. Surgery based on the described method: the prepuce has been cut lengthwise on the projection of the middle line, into each of the two edges between the external and internal skin of the prepuce ball-like element of 12 mm in diameter have been implanted. The edges of the wound have been fixed by suture forming two cleaved parts of the prepuce and the ball-like elements implanted. Additionally the ball-like elements have been fixed by π-like. Sutures removed 8 days after the wound has healed, and sexual act permitted 2 weeks after. The patient has been under medical observation for 11 months, and during the sexual act the noted the appearance or growth of the orgasm in all women partners.

EXAMPLE 2.

The patient is 32 years, married 5 years, has noted during the past three years an absense of orgasm in his wife during the sexual act. Correction carried out according to the described method. The said patient has implanted simultaneously ball-like elements and introduced an aperture in the frenulum of the prepuce. A special characteristic of the patient was the absence of the prepuce which had been removed for medical reasons in early childhood. Under local anesthesia at the distance of 10 mm from the cervix of the head under the skin of the penis to the right and to the left of the projection of the middle line were implanted 2 ball elements of 8 mm in diameter. Additionally into the area of the frenulum of the prepuce through the tissues forming it was made a pincing of the tissues using an injection needle with a synthetic thread of 1 mm in diameter, the needle was removed, the thread was fixed to the frenulum of the prepuce with 5 knots. The post-surgical period was without complications. Sexual life was taken up 3 weeks afterwards under observation for 14 months. Through the aperture formed in the frenulum of the prepuce the patient fixed from time to time the ends of the synthetic thread 10 mm long. He led a normal sexual life, during the sexual act his wife experienced orgasm each time.

The proposed method was tested on 28 patients. Observation showed that in 87% the effect was positive and consisted in the appearance and prolongation of the orgasm in women who had not experienced it before. Patients did not complain of discomfort from the implanted ball-like elements and technical difficulties linked to the taking of and to the fixing of the synthetic thread to the frenulum of the prepuce through the aperture in it were not noted.

So the proposed method of the correction of sexual disharmony between the man and the woman which appear as a result of insufficient stimulation of female erogenous zone in the area of the clitoris and of the vagina due to weak contact between the mans' genitals and the woman's erogenous zone during the sexual act can be corrected by additional structures such as implanted ball elements into the edges of the cleaved prepuce under the skin of the penis and the ends of the synthetic thread fixed to the frenulum of the prepuce through a specially formed aperture in it.

The proposed method of stimulation of female erogenous zones during the sexual act by way of a purposeful influence on the area of the clitoris and of the vagina of ball-like elements implanted into the edges of the cleaved prepuce between its external and internal skin under the skin of the body of the penis plus by way of the influence of the ends of the synthetic thread temporarily fixed to the frenulum of the prepuce through an aperture formed in it gives the possibility to achieve and prolongate the orgasm in the female partner.

The surgery is simple in technical execution, can be carried out under local anesthesia. Methods of plastic surgery are used. The implanted ball elements are made from biologically inert materials, their number, diameter are chosen in accordance with the individual anatomical characteristics of the penis and in general are 1 or 2 ball-like elements of 8 to 15 mm in diameter introduced into the cut edges of the prepuce and of 1 to 3 elements of 5 to 10 mm in diameter under the skin of the penis. The length diameter elasticity of the ends of the synthetic thread temporarily fixed to the frenulum of the prepuce are also chosen according to the individual characteristics of the patient and in general are 10 to 15 mm and 0.5–1 mm in diameter.

What is claimed is:

1. The method of sexual disharmony correction during the sexual act consisting of the following stages:

local anesthesia of part of the prepuce of the penis;

a slit of the mentioned prepuce on the aforesaid part lengthwise from its free edge into two so as the preputial sack formed by the external and internal skins of the mentioned prepuce is slit in to two parts—the left and the right;

the formation in each of these parts on the side of the mentioned slit of a cavity by way of pulling apart the mentioned external and internal skins;

an introduction into at least one of the cavities of at least one ball element at a distance of at least 5 to 7 mm from the mentioned edge of the slit;

the sewing-up of the wound between the mentioned external skin and the mentioned internal skin on each mentioned edge of the slit of the aforesaid preputial sack with the formation of two pieces of the mentioned prepuce having implanted. Therein least one of the of at least one ball element.

2. Method of claim 1, in which are implanted two ball elements, one into each of the pieces of the preputial sack.

3. Method of claim 2, in which for the aforesaid implantation ball elements of 8 to 15 mm in diameter are used.

4. Method of claim 1, in which the aforesaid ball elements after the mentioned introduction are fixed each by a like suture, which prevents its dislocation to the aforesaid stitched-up edge of the mentioned piece.

5. Method of claim 1, in which additionally the following stages are carried out:

a local anesthesia of the penis on the part along the middle line, at a distance of 5 to 15 mm from the cervix of the head of the penis;

the slitting of skin surfaces on the mentioned part under anesthesia lengthwise along the projection of the middle line at a distance from the cervix of 8 to 10 mm;

the formation of a channel and of an under-skin cavity by way of surgical access through the aforesaid slit to the right and to the left of it;

the introduction into the aforesaid cavity of at least one mentioned ball element at a distance of at least 5 to 7 mm from the mentioned line of the slit of the skin surface;

the stitching of sutures on the edges of the wounds formed by the mentioned slitting of the skin surface.

6. Method of claim 1, in which additionally the following stages are carried out:

a local anesthesia of the frenulum of the aforesaid prepuce; and the formation of a permanent aperture of 1 to 1.5 mm in diameter in the aforesaid frenulum of the prepuce.

7. The method of correction of sexual disharmony during the sexual act including the following stages:

a local anesthesia of the penis on the part along the middle line at a distance of 5 to 15 mm from the cervix of the penis;

the slitting of the skin surface on the mentioned part lengthwise along the projection of the middle line at a distance of at least 8 to 10 mm from the cervix of the head of the penis;

the formation of a channel and the formation of a cavity under the skin by way of surgical access through the mentioned slit to the left and to the right from it;

the introduction into the mentioned cavity of at least one ball element at a distance of at least 5 to 7 mm from the mentioned line of the slit of the skin surface; and the stitching of sutures on the edges of the wound formed by the aforesaid slitting of the skin surface.

8. Method of claim 7, in which for the mentioned introduction ball elements of 5 to 10 mm in diameter are used.

9. Method of claim 7, in which each mentioned ball element is fixed by suture which prevents its dislocation to the aforesaid edge of the wound.

10. The method of correction of sexual disharmony during the sexual act including the following stages:

a local anesthesia of the frenulum of the prepuce of the patients penis; and the formation of a permanent aperture of 1 to 1.5 mm in diameter in the mentioned frenulum of the prepuce.

11. Method of claim 10, in which the mentioned formation of the foresaid aperture includes the following stages:

the pincing of the tissues forming the aforesaid frenulum by an injection needle;

the pulling through the aperture of the mentioned needle of a synthetic thread of 1 to 1.5 mm in diameter;

the removal of the aforesaid injection needle; and the removal of the thread after the healing of the wound on the sides of the aforesaid aperture.

* * * * *